United States Patent
Fattman et al.

(10) Patent No.: US 9,498,372 B2
(45) Date of Patent: Nov. 22, 2016

(54) OSTOMY POUCH APPLIANCE

(75) Inventors: George Fattman, Mount Laurel, NJ (US); Gary Oberholtzer, Feasterville, PA (US)

(73) Assignee: CONVATEC TECHNOLOGIES INC., Las Vegas, NV (US)

(*) Notice: Subject to any disclaimer, the term of this patent is extended or adjusted under 35 U.S.C. 154(b) by 0 days.

(21) Appl. No.: 13/123,920

(22) PCT Filed: Nov. 30, 2009

(86) PCT No.: PCT/US2009/066100
§ 371 (c)(1),
(2), (4) Date: Apr. 13, 2011

(87) PCT Pub. No.: WO2010/060115
PCT Pub. Date: May 27, 2010

(65) Prior Publication Data
US 2011/0213321 A1  Sep. 1, 2011

Related U.S. Application Data

(60) Provisional application No. 61/116,173, filed on Nov. 19, 2008.

(51) Int. Cl.
*A61F 5/448* (2006.01)
*A61F 5/443* (2006.01)

(52) U.S. Cl.
CPC .............. *A61F 5/443* (2013.01); *A61F 5/448* (2013.01)

(58) Field of Classification Search
USPC .................................................. 604/344, 244
See application file for complete search history.

(56) References Cited

U.S. PATENT DOCUMENTS

| | | | | |
|---|---|---|---|---|
| 2,796,063 A | * | 6/1957 | Smelser | A61F 5/448 604/342 |
| 3,948,256 A | * | 4/1976 | Schneider | A61F 5/448 604/344 |
| 4,294,252 A | * | 10/1981 | Einset | A61F 5/448 604/345 |
| 4,359,051 A | | 11/1982 | Oczkowski | |
| 4,551,490 A | | 11/1985 | Doyle | |
| 6,537,261 B1 | * | 3/2003 | Steer | A61F 5/448 604/342 |
| 6,840,924 B2 | | 1/2005 | Buglino | |
| 6,929,627 B2 | * | 8/2005 | Mahoney | A61F 5/445 604/332 |

(Continued)

FOREIGN PATENT DOCUMENTS

| | | |
|---|---|---|
| WO | WO2004084777 | 10/2004 |
| WO | WO2006035014 | 4/2005 |
| WO | WO-2008/124717 A2 | 10/2008 |

OTHER PUBLICATIONS

PCT/US2009/06100 International Search Report Mailed Feb. 12, 2010.

*Primary Examiner* — Adam Marcetich
*Assistant Examiner* — Guy K Townsend
(74) *Attorney, Agent, or Firm* — Wilson Sonsini Goodrich & Rosati

(57) ABSTRACT

A coupling assembly for fastening an adhesive wafer to an ostomy appliance device, the coupling assembly including a captive connection between the adhesive wafer and ostomy appliance that permits captive relative displacement between the entire adhesive wafer and the entrance aperture of the appliance, to facilitate access to the wafer from the non-body-contacting side. The coupling assembly further comprises a fixation coupling for fixing the adhesive wafer in the operative position.

10 Claims, 16 Drawing Sheets

(56) References Cited

U.S. PATENT DOCUMENTS

| | | | |
|---|---|---|---|
| 7,367,965 B2* | 5/2008 | Poulsen | A61F 5/441 604/322 |
| 7,422,578 B2* | 9/2008 | Shan | A61F 5/448 604/332 |
| 7,517,339 B2* | 4/2009 | Pedersen | A61F 5/448 604/344 |
| 2004/0184876 A1* | 9/2004 | Hessel | A61F 5/448 403/326 |
| 2005/0085779 A1* | 4/2005 | Poulsen | A61F 5/441 604/332 |
| 2005/0113770 A1* | 5/2005 | Pedersen | A61F 5/448 604/332 |
| 2007/0005032 A1* | 1/2007 | Shan | A61F 5/448 604/342 |
| 2007/0005033 A1* | 1/2007 | Ciok | A61F 5/443 604/344 |
| 2007/0255240 A1* | 11/2007 | Ciok | A61F 5/445 604/339 |
| 2011/0213322 A1* | 9/2011 | Cramer | A61F 5/443 604/344 |

* cited by examiner

OSTOMY POUCH APPLIANCE

FIELD OF THE INVENTION

The present invention relates to an ostomy appliance, for example, an ostomy pouch. In particular, the invention relates to a so-called one-piece ostomy appliance in which a moldable adhesive body fitment is permanently attached to the pouch.

BACKGROUND TO THE INVENTION

Modern ostomy appliances are commonly attached to the body by means of an adhesive wafer. The adhesive wafers most commonly used are designed to have a predetermined, fixed shape. The wearer cuts the central opening of the adhesive wafer to match his or her stoma size and shape, using scissors to cut along guidance lines that are pre-printed on the adhesive release sheet for certain standard sizes.

In a so-called one-piece appliance, the adhesive wafer is permanently attached to the appliance, to the extent that the adhesive wafer cannot easily be separated without risk of damaging the appliance. A one-piece appliance is intended to be used as an integral unit. A complaint sometimes made about one-piece appliances is that it is not always easy for elderly, visually impaired, or non-dexterous persons to adapt the size of the central opening in the adhesive wafer, because the appliance obstructs access from one side.

In a so-called two-piece appliance, the adhesive wafer forms part of a separate body fitment component that is attached by a releasable coupling. A two-piece appliance permits the body fitment to be separated from the appliance without damage, so that at least one of the components continues to be functionally usable. For example, the body fitment may remain in place on the body, and a replacement pouch mounted in place of a used pouch. While a two-piece appliance allows better access for adapting the wafer, a common complaint about two-piece appliances is that it is not always easy to align the components, particularly for elderly, visually impaired or non-dexterous users.

U.S. Pat. No. 6,840,924 describes an improved one-piece or two-piece ostomy appliance including a moldable adhesive, in which at least a portion of the adhesive can be manually molded by the wearer, to provide a custom fit around the stoma. This alternative way of customizing the wafer offers the prospect of a better fit around the stoma than that obtainable by cutting along standard size guidelines. Achieving a good fit is desirable in order to reduce the exposure of the peristomal skin to stool exiting the stoma. Peristomal skin may be quite sensitive, and vulnerable to irritation or infection when contacted by stool. Stool exiting the stoma may contain digestive juices from the body, and such juices can also attack the peristomal skin resulting in excoriation. Contact by stool also progressively reduces the effectiveness of the adhesive. However, stomas have many different sizes and shapes. The advantage of a moldable adhesive as taught in U.S. Pat. No. 6,840,924 is that the user can mold the adhesive to closely match the exact size and shape of the stoma.

In a form in which the appliance of U.S. Pat. No. 6,840,924 is implemented as a two-piece ostomy appliance, the wearer is able to access the moldable adhesive from both sides, including the non-body-contacting side, when the pouch is separated from the body fitment. This can enable the wearer easily to mold the adhesive, e.g., by folding or rolling it back from the non-body-contacting side. However, access is more restricted when implemented as a conventional style of one-piece appliance, as illustrated by the pouch 20 in FIG. 1 of the accompanying drawings. The wearer can only access the moldable adhesive 21 to mold the stomal aperture from a body-contacting side 22, and not from an opposite non-body-contacting side 23 that is covered by the immovable pouch 20. This makes molding the adhesive more difficult, and means that the shape and size of the aperture might not be as accurate as would be when the adhesive is accessible from both sides.

WO2004/084777 and WO2006/035014 describe alternative one-piece ostomy pouches in which an adhesive wafer is attached to the pouch using two different types of attachment extending in complementary first and second angular sectors or arcs that together extend completely around the stoma aperture. In the first angular sector around the stoma aperture, the wafer is permanently attached immovably. In the second angular sector around the aperture, the wafer is initially unattached or is releasably attachable. The second angular sector is said to permit the pouch to be partly folded ajar of the wafer in the limited region of the second sector, allowing access through the gap created between the wafer and the pouch. This access is said to facilitate cutting the adhesive, or fitting a separate sealing member, or removal and fitting of a separate disposable inner pouch. However, such a solution illustrates the inherent incompatibilities associated with trying to combine two-piece behavior with an immovable body fitment of a one-piece appliance. With such a solution, the first sector in which the body fitment is immovable, hinders access to the body fitment because the pouch cannot be folded away in this region. Unless the second sector is made exceptionally large, access to the adhesive as a whole may still be restricted, making it difficult for an elderly or non-dexterous person to use the appliance. Additionally, there may be vulnerabilities in the seal between the faceplate and the pouch at (i) the points at where the first and second sectors meet around the periphery of the stoma aperture, and/or (ii) at the folding notches or creases of the stiffening ring that is used, in view of the discontinuities which are inevitable at all of these points.

A further manufacturing limitation of the conventional one-piece style of FIG. 1, and the alternative arrangements described in WO2004/084777 and WO2006/035014, is that the pouch 20 typically needs to be dimensioned to extend beyond the extremity of the adhesive 21 on all sides. This geometry is believed present in all of the mass-produced one-piece pouches currently available, and is a consequence of the manufacturing techniques used. The techniques typically require space for manufacturing equipment to come into intimate contact with the material for the pouch walls 24, 25 to form a peripheral weld 26 and stamp the material, after the adhesive 21 has already been attached in its operative position around the entrance aperture 27. The pouch 20 usually extends significantly below the entrance aperture 27 to provide the main collection volume of the pouch 20, and so this geometry poses no problems for the lower portion of the pouch. However, the need for the pouch 20 also to extend upwardly above, and/or to either side of, the adhesive 22 results in unused headspace 28. Such headspace 28 is undesirable because it cannot easily be used as part of the collection volume of the pouch, and it merely adds undesirably to the size of the pouch 20.

The present invention provides surprising solutions to these problems

SUMMARY OF THE INVENTION

One aspect of the present invention provides a coupling device for fastening an adhesive wafer to an ostomy appliance, the coupling device comprising:

a limited motion connection between the adhesive wafer and the appliance that permits relative displacement between (i) substantially the entire adhesive wafer and (ii) the entrance aperture of the appliance, the limited motion connection guiding said relative displacement along a limited motion locus, between (a) an operative position and an access position; and a fixation coupling for fixing the adhesive wafer and the appliance when in the operative position.

In the operative position, the adhesive wafer is superposed around the entrance aperture of the appliance, and an adaptable region of the adhesive wafer is shrouded by the appliance on the non-body-facing side. The access position provides access to the adaptable region from the non-body-facing side.

Such an arrangement can guide alignment of the wafer and the appliance to the operative position, making such alignment much easier for elderly, non-dexterous, or visually impaired persons. At the same time, the limited motion coupling permits relative displacement of substantially the entire adhesive wafer with respect to the entrance aperture, allowing access for adapting the adhesive wafer to the size and/or shape of the user's stoma. The limited motion connection may comprise an articulating link, the articulation defining the locus of limited motion.

This aspect of the invention may be used with a one-piece appliance to enhance access to the adhesive wafer, while avoiding problems of a wholly or partly immovable adhesive wafer as in the prior art. The ability to relatively displace the entire adhesive wafer with respect to the entrance aperture of the pouch may permit easier adaptation of the wafer (whether by forming, cutting or shaping the stomal aperture, or by fitting and/or shaping a separate sealing member at the stomal aperture).

Likewise, this aspect of the invention may also be used with a two-piece appliance to facilitate easier alignment of the components, without significantly reducing ease of access for adapting the wafer to the size and/or shape of stoma, nor detracting from the ability to position the body-fitment on the body before fixing the appliance in the operative position with respect to the body fitment. The limited motion connection and the fixation coupling may comprise releasable coupling portions.

A second aspect of the invention provides a one-piece appliance comprising a captive connection permanently attaching the adhesive wafer captively to the appliance in a manner permitting relative displacement between the entrance aperture of the pouch, and substantially the entire adhesive wafer.

The captive connection defines a range of captive movement between the appliance and the adhesive wafer. The captive range of movement includes:

(i) a superposed operative position in which the adhesive wafer is superposed around the entrance aperture, and an adaptable portion of the adhesive wafer is shrouded on the non-body-facing side by the appliance; and (ii) a non-superposed position providing access from the non-body-facing side to the adaptable portion of the adhesive wafer.

The captive connection may be a limited motion connection as explained above to provide alignment guidance, or the captive connection may be a tether without defining a specific guidance locus. In either case, the use of a captive connection facilitates easier access to the adhesive wafer of a one-piece appliance, while avoiding problems of a wholly or partly immovable adhesive wafer as in the prior art. The ability to relatively displace the entire adhesive wafer with respect to the entrance aperture of the pouch may permit easier adaptation of the adaptable portion (whether by forming, cutting or shaping the stomal aperture, or by fitting and/or shaping a separate sealing member at the stomal aperture). The captive connection also enables avoidance of the potential sealing issues described above at discontinuities where immovable and movable sectors both directly border the entrance aperture.

The captive connection can also enable an adhesive wafer to be used that, when in the operative position around the stomal aperture, extends all of the way up to, or even beyond, the periphery of the pouch. Such a geometry becomes easily realisable because the captive coupling permits the adhesive wafer to be positioned in, or displaced to, an alternative position within the pouch profile, to enable the peripheral welding and stamping operation to be carried out around the pouch profile.

In either aspect of the invention, the ostomy appliance may be an ostomy pouch, or some other ostomy device such as a stoma port or a controlled evacuation device.

As used herein the term "permanently attached" (or like phrases) means that the pieces are attached so strongly that they cannot be separated without breakage or damage that prevents reattachment without additional equipment.

While features believed to be of special significance have been identified above and the appended claims, claim protection may be sought for any novel feature or idea described herein and/or illustrated in the drawings, whether or not emphasis has been placed thereon.

DETAILED DESCRIPTION OF THE PREFERRED EMBODIMENTS

Figure 1:
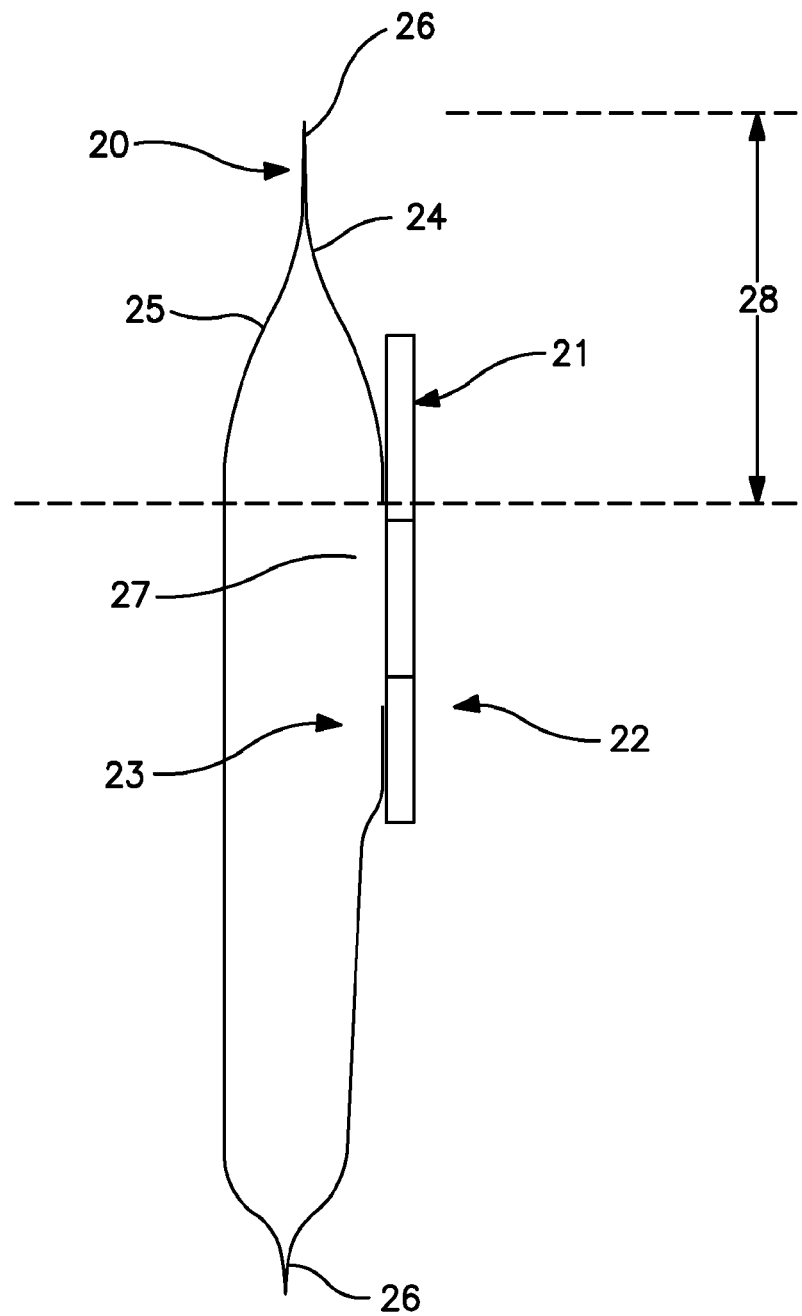
FIG. 1 is a schematic side-sectional view through a prior art example one-piece ostomy pouch appliance.
Figure 2:
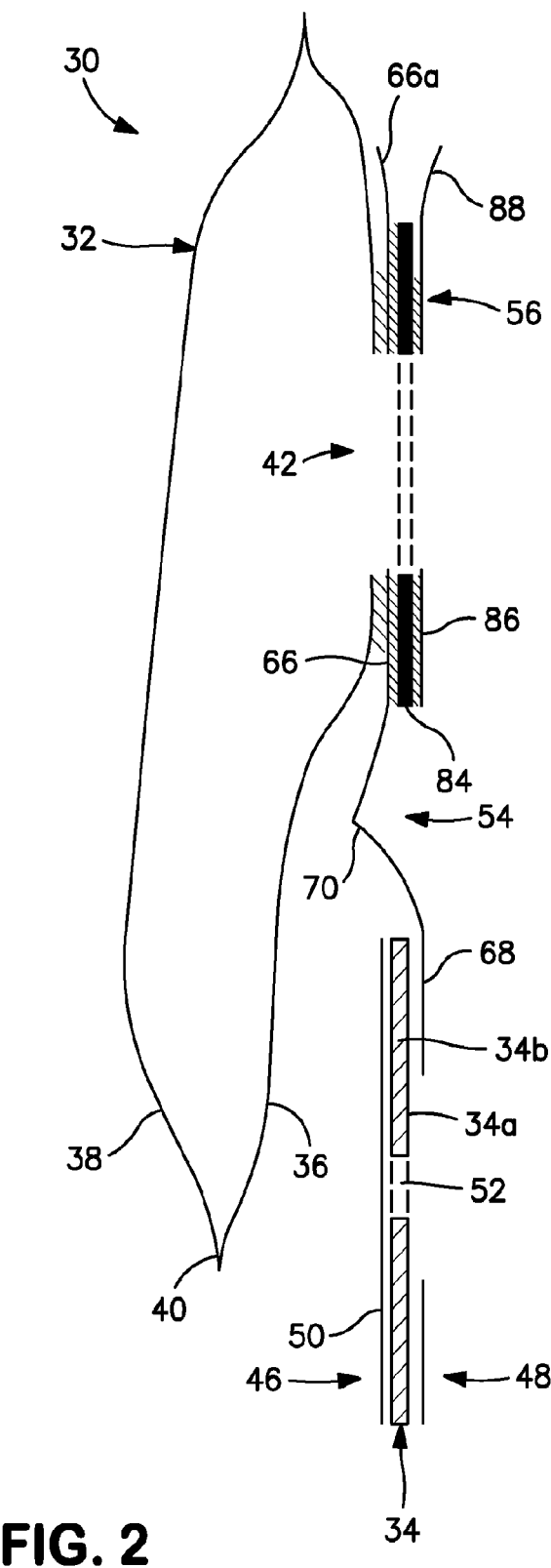
FIG. 2 is a schematic sectional view through a first embodiment of the invention shown in the access position.

Referring to FIGS. 2-8, a first embodiment illustrates a one-piece ostomy appliance 30 comprising an ostomy pouch 32 and an adhesive wafer 34 permanently attached to the ostomy pouch 32. The ostomy pouch 32 may be any of a colostomy pouch, a urostomy pouch and an ileostomy pouch.

The ostomy pouch 32 generally comprises a rear wall 36 and a front wall 38. The front and rear walls 36, 38 are made of flexible plastic films that are generally impermeable to liquid and gas. A suitable film includes, for example, a laminate of one or more layers of ethylene vinyl acetate (EVA), and one more layers of a gas barrier material, such as poly(vinylidene chloride) (PVDC) or poly(vinylidene fluride) (PVDF). The walls 36, 38 are welded together around a mutual periphery seam 40. The rear wall 36 comprises a stomal or entrance aperture 42 through which stomal effluent enters the pouch 32, in use. The pouch 32 optionally further comprises a deodorizing filter and vent (not shown) for deodorizing and venting flatus. Additionally or alternatively, the pouch 32 optionally further comprises a comfort panel (not shown) on the exterior surface of one or both of the walls 36, 38.

Figure 3:
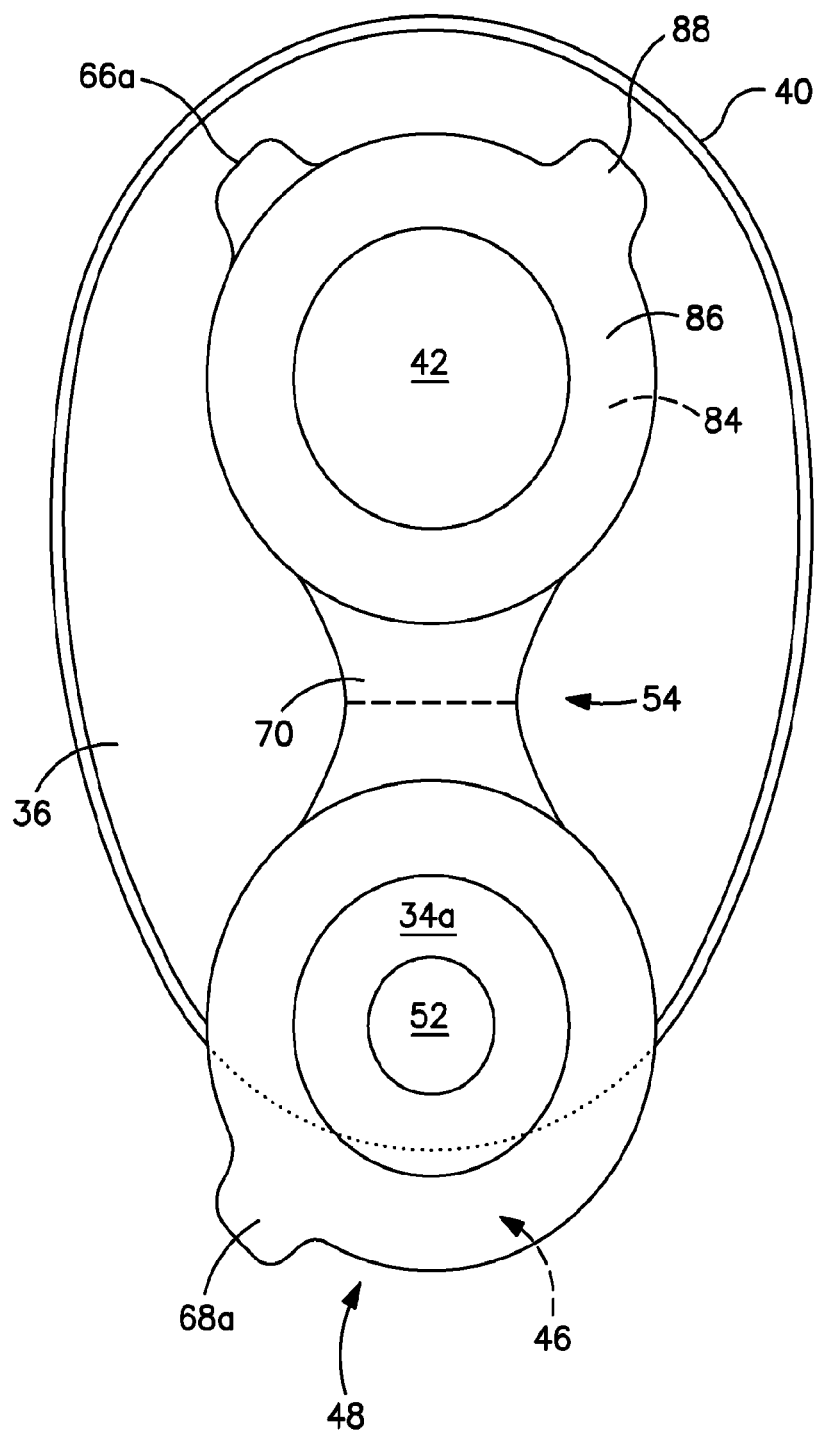
FIG. 3 is a schematic rear view of the first embodiment in the access position.
Figure 4:
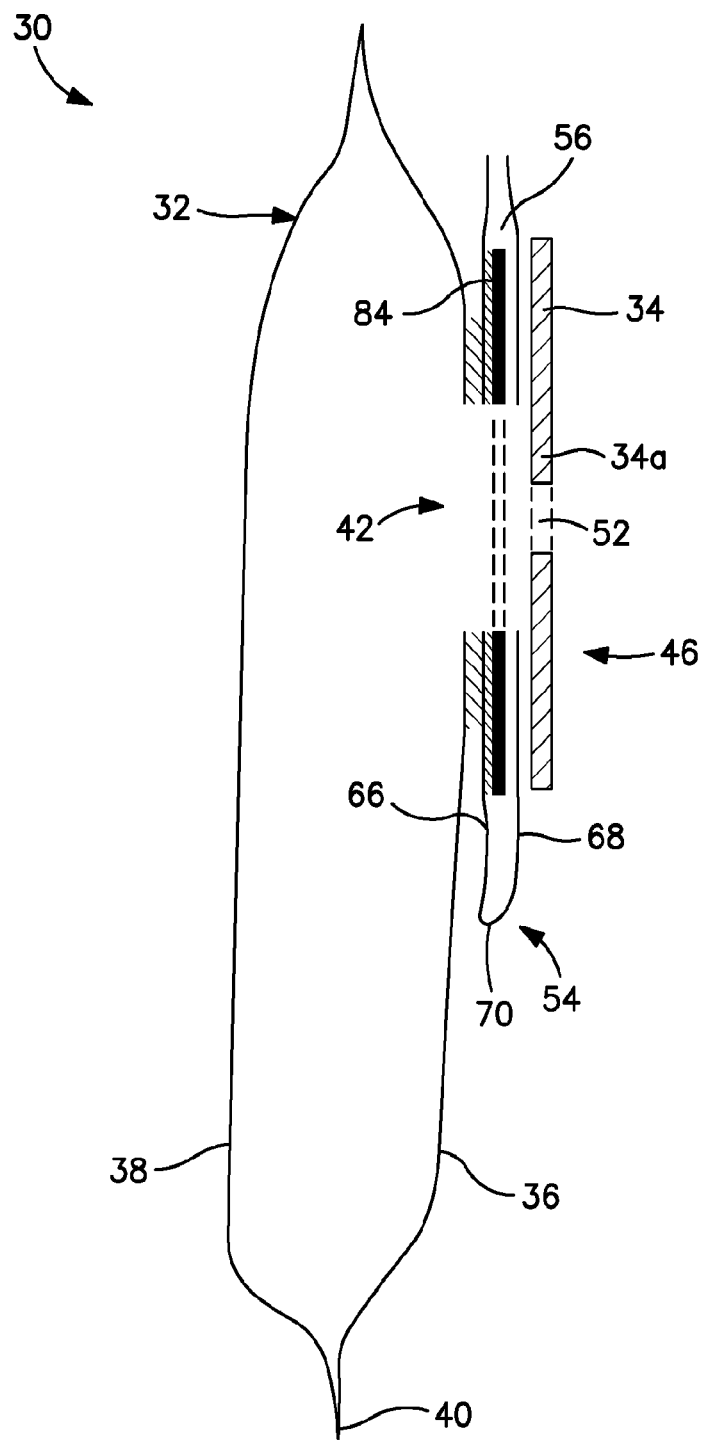
FIG. 4 is a schematic sectional view through the first embodiment shown in the operative position.
Figure 5:
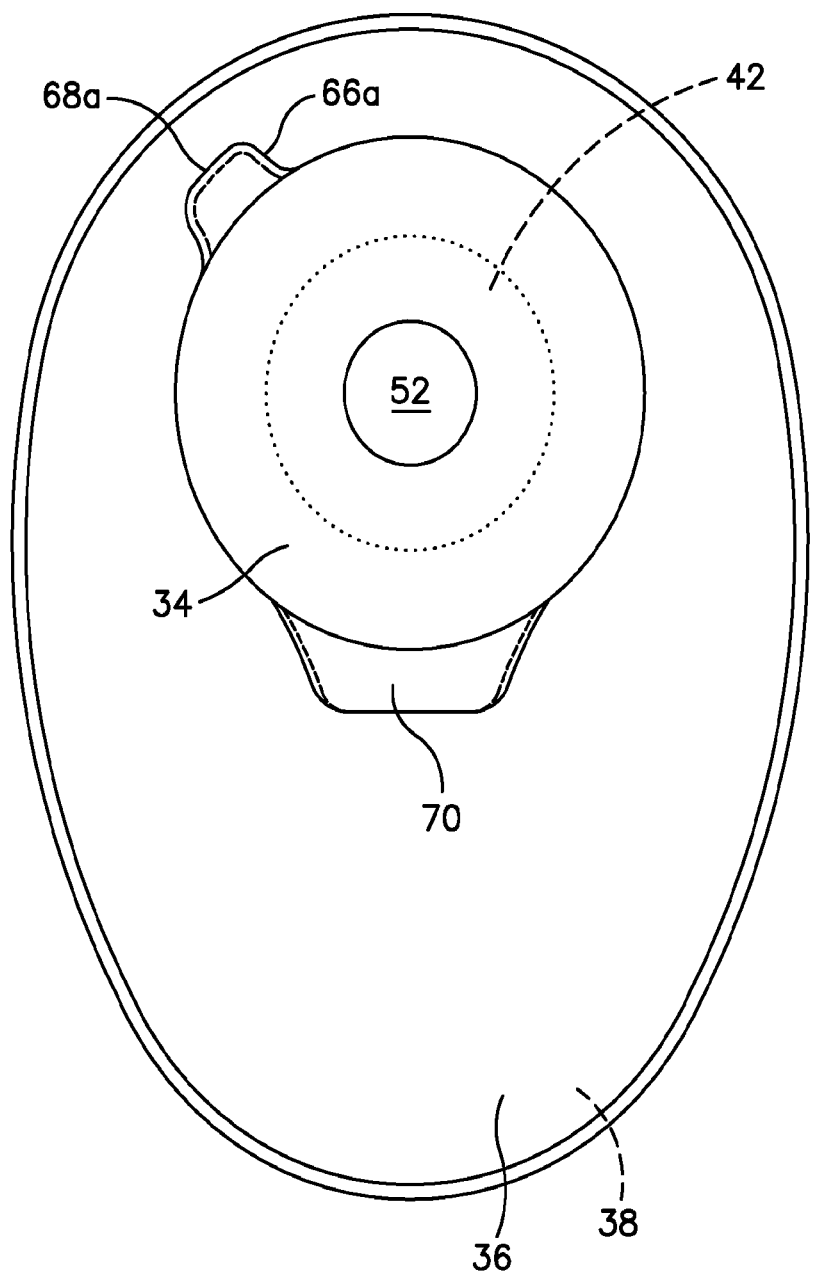
FIG. 5 is a schematic rear view of the first embodiment in the operative position.
Figure 6:
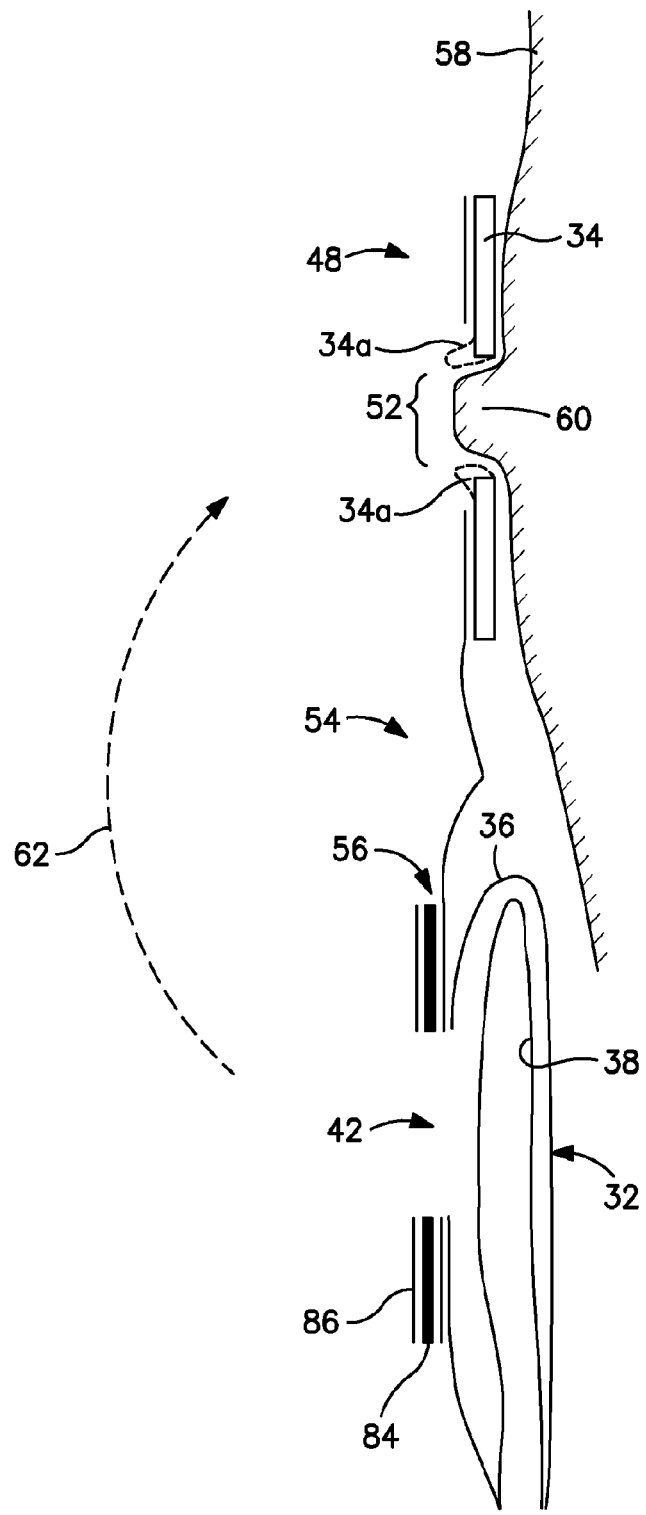
FIG. 6 is a schematic sectional view showing an example of fitting the appliance of the first embodiment to the body.

The adhesive wafer 34 comprises a skin compatible adhesive for attaching the appliance to peristomal skin, in use. The adhesive wafer 34 generally has a body-facing side 46 for facing towards and contacting the skin in use, and a non-body-facing side 48 that faces in the opposite direction. The body-facing side 46 may initially be protected by a release sheet 50, for example, of silicone sheet or silicone-coated sheet. The adhesive wafer 34 is adaptable to enable a stomal aperture 52 to be formed and/or customized to match the size and shape of the ostomate's stoma 60 (FIG. 6). Various techniques are envisaged for implementing such adaptation. In one form, the adhesive wafer 34 is of a moldable or shapeable type, in which at least a portion 34a of the adhesive is moldable or shapeable by manual manipulation. The adhesive wafer 34 may have a pre-formed starter stomal aperture 52 around which at least an inner peripheral region of adhesive wafer portion 34a is moldable or shapeable. Alternatively, if no starter stomal aperture 52 is provided, the adhesive may be of a type permitting a user to manually create and shape a suitable aperture 52 therein. The moldability and/or shapeability enables a close or snug fit to be achieved around the stoma 60. A snug fit is highly desirable, in order (i) to protect the ostomate's peristomal skin 62 from irritation and excoriation by contact with stool exuding from the stoma 60, as well as (ii) to form a seal that obstructs stomal effluent from contaminating the adhesive surface on the body-facing side 46, which might otherwise reduce the wear-life of the appliance 30. The adhesive wafer 34 may, for example, be of the type described in the aforementioned U.S. Pat. No. 6,840,924. Such an adhesive wafer 34 enables shaping while retaining a sheet-like form. The adhesive wafer 34 comprises a laminate structure including (i) plural layers of adhesive, and/or (ii) at least one layer of adhesive reinforced by at least one layer of plastics film. The stomal aperture 52 in the adhesive wafer 34 can be expanded to a customized shape and/or size by bending and rolling the adhesive wafer 34 back on itself around the stomal aperture 52, as illustrated in FIG. 3. Typically, the adhesive wafer 34 is rolled back on the non-body-facing side 48 of the adhesive wafer 34, and this operation is most easily and accurately carried out from the non-body-facing side 48. Alternatively, the adhesive may be of a flowable or extrudable mass type (not shown). Again, such adaptation is most easily and accurately carried out having access to at least the non-body-facing side 48 (preferably to both sides 46, 48).

In an alternative form, the stomal aperture 52 may be adapted or customized by fitting a separate sealing member (not shown) that seals insides the stomal aperture 52. Such a sealing member is also best fitted to the non-body-facing side 48 of the adhesive wafer 34, so as not to interfere with the adhesive interface between the body and the adhesive wafer 34 on the body-facing side 46.

The present embodiment facilitates access to the non-body-facing side 48 of the adhesive wafer 34 because, initially, the adhesive wafer 34 is not attached immovably around the entrance aperture 42. Instead, the appliance 30 further comprises one or both of:

(a) a captive connection 54 permanently attaching the adhesive wafer 34 captively to the pouch 32 in a manner permitting relative displacement between (i) substantially the entire entrance aperture 42 of the pouch 32, and (ii) substantially the entire adhesive wafer 34;

(b) a fixation coupling 56 for fixing the adhesive wafer 34 to the pouch 32, when desired, in an operative position around the entrance aperture 42.

Prior to first use, the captive connection 54 permits relative displacement between the adhesive wafer 34 and the pouch 32 over a captive range of movement. The captive range of movement includes:

(i) a superposed operative position in which the adhesive wafer 34 is superposed around the entrance aperture 42, and the adaptable portion 34a of the adhesive wafer 34 is shrouded on the non-body-facing side 48 by the pouch 32; and (ii) an access position providing access from the non-body-facing side 48 to the adaptable portion 34a of the adhesive wafer 34.

Such an arrangement permits easy maneuvering of the pouch 32 and the adhesive wafer 34, one with respect to the other, to provide convenient access to the adhesive wafer 34 from the non-body-contacting side 48, substantially without obstruction by the pouch 32. Preferably, the user has access from both sides 46, 48. The user is therefore able to form and/or shape and/or size the stomal aperture 52 easily without needing considerable dexterity to manipulate the appliance 30.

In the illustrated forms, the captive connection 54 is preferably implemented in the form of a limited motion connection that guides the relative displacement along a predetermined locus or path of motion. Such a limited motion connection can guide the motion between the adhesive wafer 34 and/or pouch 32 to the operative position, at least in one dimension or degree of freedom. This can enable easier alignment of the adhesive wafer 34 with respect to the pouch 32 than, for example, a conventional two-piece appliance in which the adhesive wafer 34 is generally freely movable with respect to the appliance prior to fixation.

The user can decide how best to fit the appliance 30 to the body. In one technique, the user adapts the adhesive wafer 34 substantially entirely before fitting the appliance 30 to the body. Having adapted the adhesive wafer 34 in the non-superposed position, the user moves the adhesive wafer 34 to its operative position (FIGS. 4 and 5) prior to fitting the appliance 30 to the body. The adhesive wafer 34 is fixed in position by the fixation coupling 56, after which the appliance 30 is fitted to the body in the style of a conventional one-piece appliance.

In another technique that may be preferred by many users (illustrated in FIG. 6), the adhesive wafer 34 is fitted to the body 58 before the adhesive wafer 34 is fixed in its operative position with respect to the pouch 32. This technique permits the user to adapt or further adapt the stomal aperture 52 in situ around the stoma 60, accessing the adhesive wafer 34 from the non-body-facing side 48. The flexibility of the pouch 32 may enable the pouch 32 to be easily folded away from the entire adhesive wafer 34, and to expose the non-body-contacting side 48 of the adhesive wafer 34 to the user. Once the user is content with the custom fit of the stomal aperture 52 to his or her stoma 60, the user then moves or unfolds the pouch 32, to bring the entrance aperture 42 to the operative position with respect to the adhesive wafer 34 (indicated by arrow 64). If a limited motion connection is implemented, the connection guides the motion to the operative position, greatly assisting the user. Once in the operative position, the pouch 32 is then fixed relative to the adhesive wafer 34 by the fixation coupling 56.

Various ways are envisaged for implementing (i) the captive connection 54, and (ii) the fixation coupling 56.

The captive connection 54 may be at least one of flexible, bendable, rotatable, pivotable, twistable, and/or stretchable to permit the relative displacement. In an alternative form, the captive connection 54 could be substantially rigid, and the relative displacement provided by the flexibility of the pouch 32 itself.

In the form illustrated in FIGS. 1-7, the captive connection 54 comprises a bendable and/or hinged connection. The captive connection 54 comprises a first attachment portion 66, a second attachment portion 68, and a bendable or hinged joint 70 between the two portions 66, 68. The captive connection 54 may be made of a single piece of material, and the bendable joint 70 may be implemented as an integral hinge, such as a folding or bendable portion, or a living hinge, or a region that is any of: weakened, thinned, perforated and/or scored. For example, the captive coupling 54 may be made of a single piece of plastics film. The film may be flexible, and optionally weakened to define the joint 70 at which the film is encouraged to bend.

Figure 7:
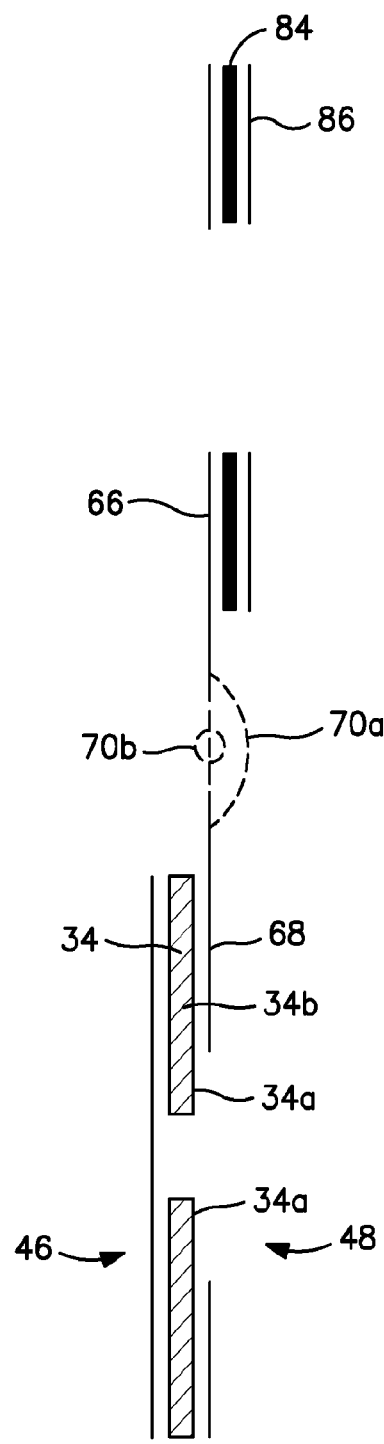
FIG. 7 is a schematic sectional view showing, in isolation, a modified form of the captive connection of the first embodiment.

Alternatively, referring to FIG. 7, the two portions 66, 68 may be distinct members joined by a hinge piece 70a or 70b. The hinge piece 70a may, for example, be of flexible material, such as a fabric or flexible film. Alternatively, the hinge piece 70b may be a hinge mechanism, possibly including a rotating pivot.

In the forms illustrated in FIGS. 1-7, the joint 70 permits relative displacement about an axis that extends generally parallel to a major plane of the adhesive wafer 34 and/or of the pouch 32 (when straight). One advantage of this arrangement is that, when the adhesive wafer 34 is displaced with the respect to the entrance aperture 42, the non-body-facing side 48 of the adhesive wafer 34 is automatically exposed and presented to the user. For example, with relative displacement of about 180 degrees (FIGS. 2, 3, 6 and 7), the non-body-contacting side 48 is presented facing the user on the rear pouch wall 36. Such geometry provides exceptionally convenient access to the non-body-contacting side 48 of the adhesive wafer 34, even with the adhesive wafer 34 permanently attached to the pouch 32 as a one-piece appliance. The user is thus able easily to access the adhesive wafer 34 from at least the non-body-contacting side 48 in order to permit the most accurate and versatile adaptation of the stomal aperture 52.

The first attachment portion 66 is configured to be attached permanently to the pouch 32, for example, by welding or by strong adhesive. The first attachment portion 66 could be attached to either of the pouch walls 36, 38, and/or at the seam 40. In the illustrated form, the first attachment portion 66 is attached to the rear wall 36 adjacent to the entrance aperture 42. The first attachment portion 66 comprises a generally hollow form (preferably closed-loop in shape) that extends at least partly (and preferably entirely) around the entrance aperture 42. The first attachment portion 66 may serve to reinforce the pouch wall material around the entrance aperture 42, to prevent wrinkling or stretching, and to provide a good surface for the fixation coupling 56.

The second attachment portion 68 is configured to be attached permanently to the adhesive wafer 34, for example, by welding or by strong adhesive action (for example, between the adhesive of the adhesive wafer 34 and the second attachment portion 68). In the illustrated form, the second attachment portion 68 is attached to the adhesive wafer 34 on the non-body-contacting side 48, in a peripheral region 34b surrounding the inner peripheral region 34a. The second attachment portion 68 may have any desired form. As illustrated, the second attachment portion 68 comprises a generally hollow form (preferably closed-loop in shape) that extends at least partly (and preferably entirely) around the stomal aperture 52 and/or adaptable region 34a.

The captive connection 54 may resemble a figure-of-eight shape, comprising two closed-loop forms disposed side-by-side (either immediately adjacent, or slightly separated), and coupled by the joint 70.

The first and second attachment portions 66, 68 are typically of about the same size, i.e., having the same size of inner and/or outer diameter so as to fit substantially back to back in the operative position. Each attachment portion may have a respective tab 66a, 66b, positioned so that the tabs 66a, 66b generally entirely overlap each other in register in the operative position. The tabs 66a, 66b permit easy manipulation of the captive connection 54.

Figure 8:
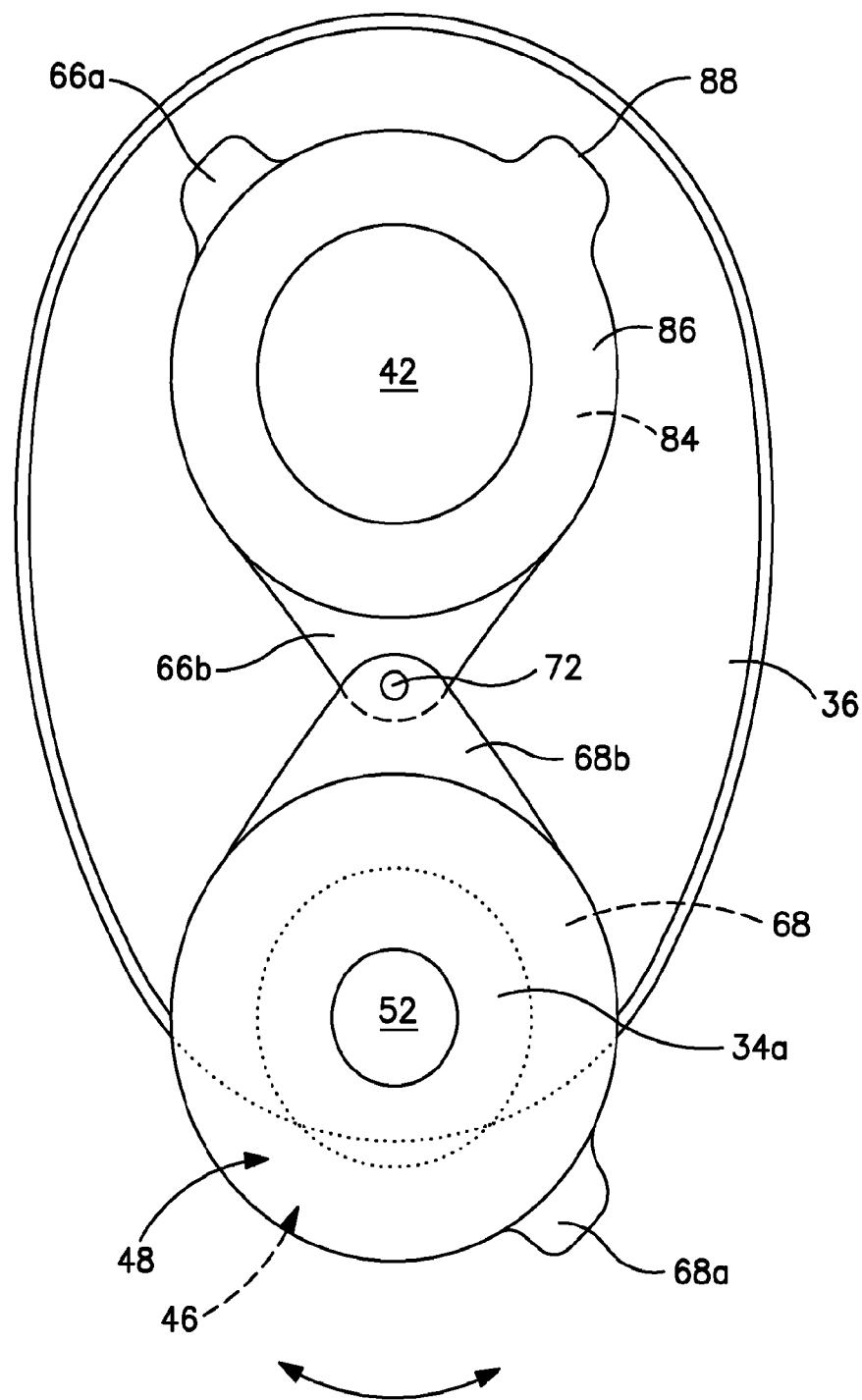
FIG. 8 is a schematic rear view showing a second embodiment in the access position.
Figure 9:
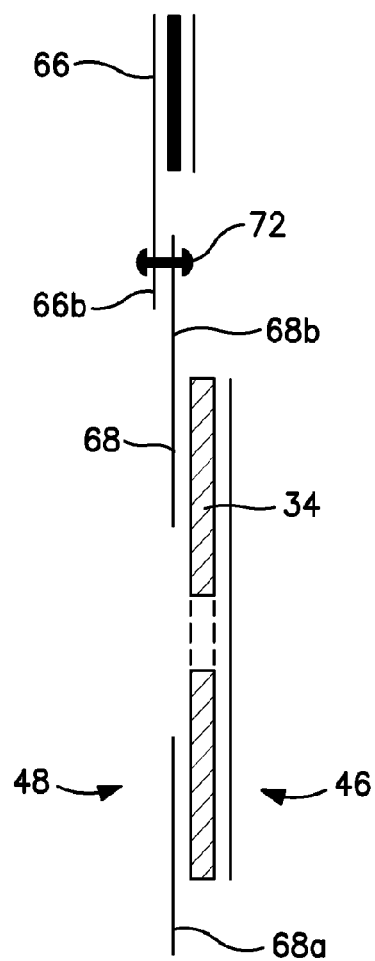
FIG. 9 is a schematic sectional view showing, in isolation, the captive connection of the second embodiment, in its access position.

Referring to FIGS. 8 and 9, an alternative joint 70 comprises a pivot 72 that permits relative pivotable movement between the pouch 32 and the adhesive wafer 34 in a plane generally parallel to the plane of the pouch 32 (when straight) and/or generally parallel to a major plane of the adhesive wafer 34. The pivot 72 may define a pivot axis that is generally perpendicular to the plane of the pouch 32 (when straight) and/or generally perpendicular to a major plane of the adhesive wafer 34. The pivot 72 may comprise a pin, lug or rivet received in apertures in overlapping tabs 66b, 68b of the first and second attachment portions 66, 68. In the illustrated form, the first and second attachment portions 66, 68 are each closed-loop in shape. The pivot 72 permits the first and second attachment portions 66, 68 to be moved from generally concentric, superposed relation (corresponding to the operative position) to generally non-concentric, non-superposed relation, permitting access to the adhesive wafer 34 away from the entrance aperture 42. As can be seen from FIG. 9, there is no reversal of the positions of the body-facing side 46 and non-body-facing side 48 when the captive coupling is rotated. Nevertheless, the flexibility of the plastics films forming the first and second attachment portions 66, 68 permits easy access to the non-body-facing side 48 when the wafer 34 is rotated away from the operative position.

Figure 10:
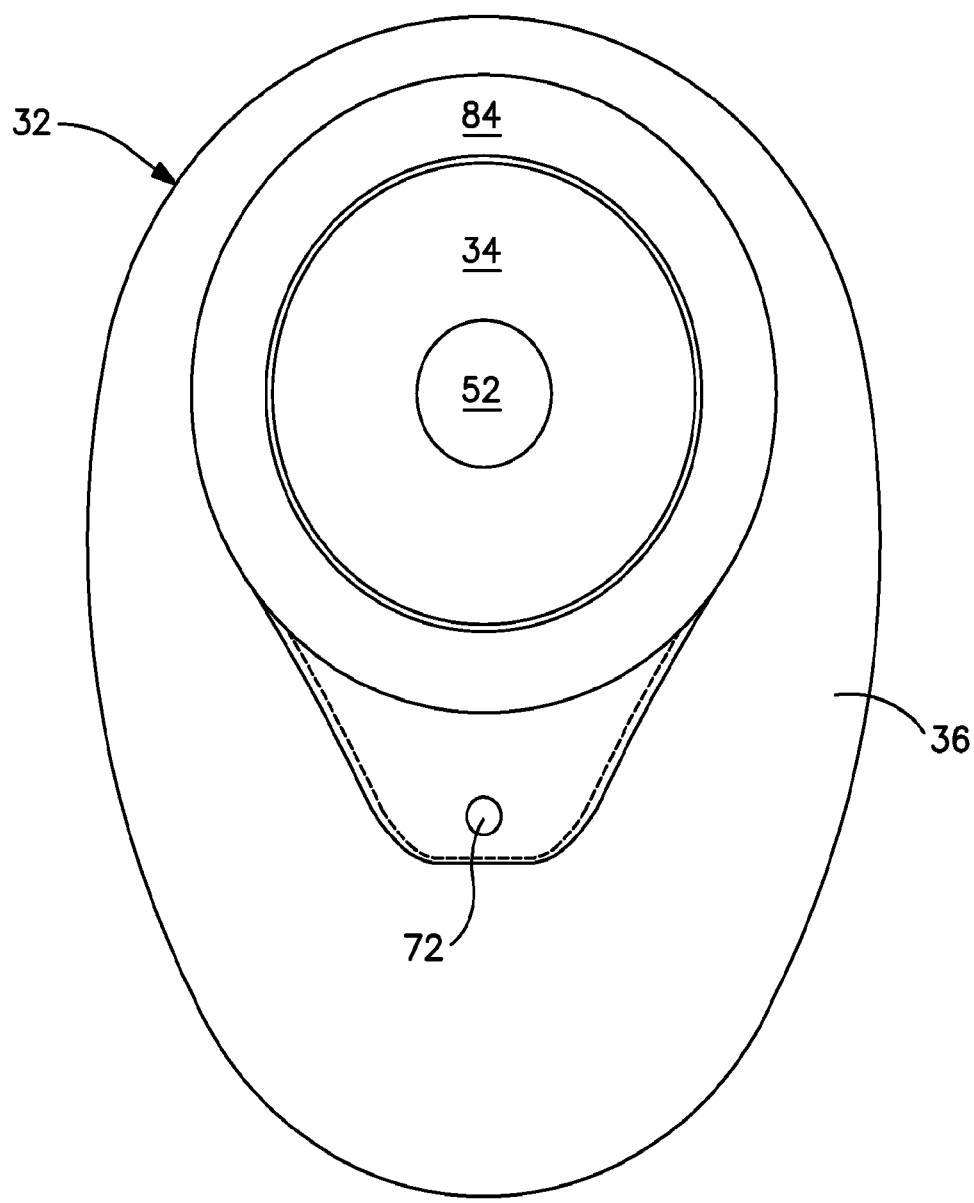
FIG. 10 is a schematic rear view showing a modification of the second embodiment in the operative position.

FIG. 10 shows a modification of the second embodiment that provides an additional positive fit when the adhesive wafer 34 is rotated to its operative position. The adhesive wafer 34 is dimensioned so that its outer diameter is slightly smaller than the inner diameter of the fixation coupling adhesive 84 carried on the first attachment portion 66, enabling the adhesive wafer 34 to nest at least partly within the aperture of the fixation coupling adhesive 84. This nesting provides additional tactile information to the user that the adhesive wafer 34 is correctly aligned at the operative position. The same technique of a nested fit may also be used with the other embodiments described herein.

Figure 11:
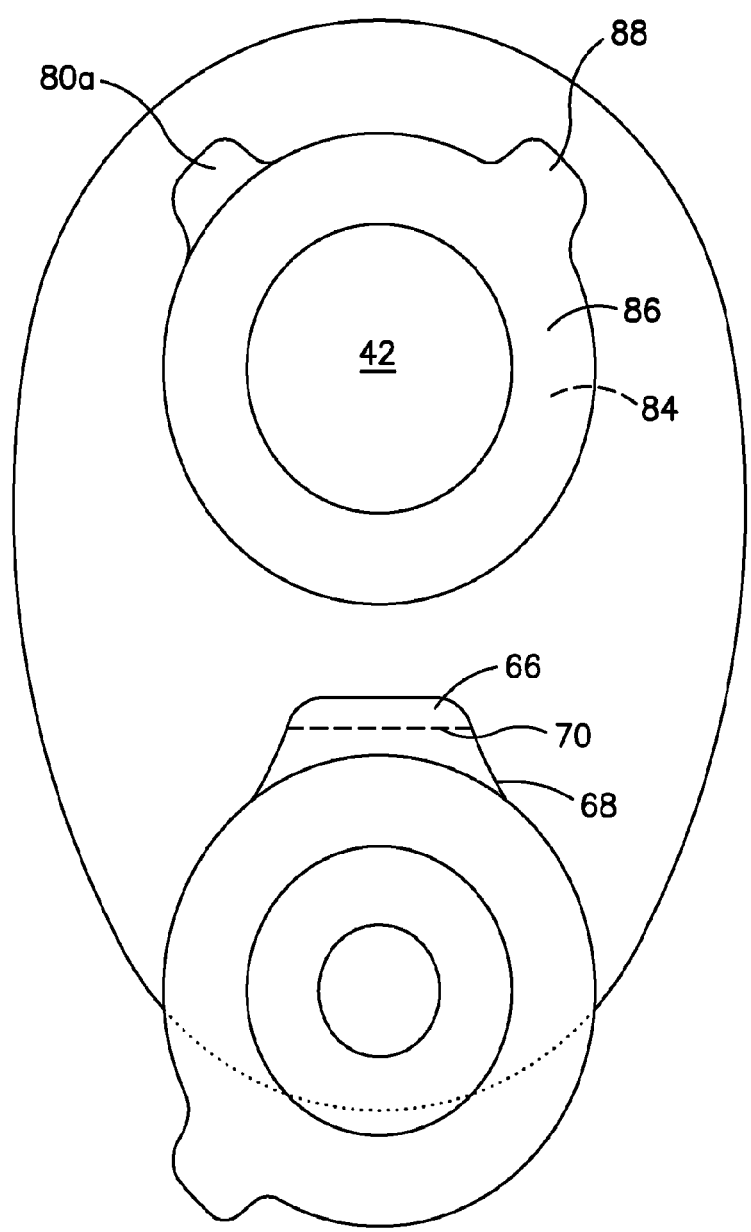
FIG. 11 is a schematic rear view showing a third embodiment of appliance in its access position.
Figure 12:
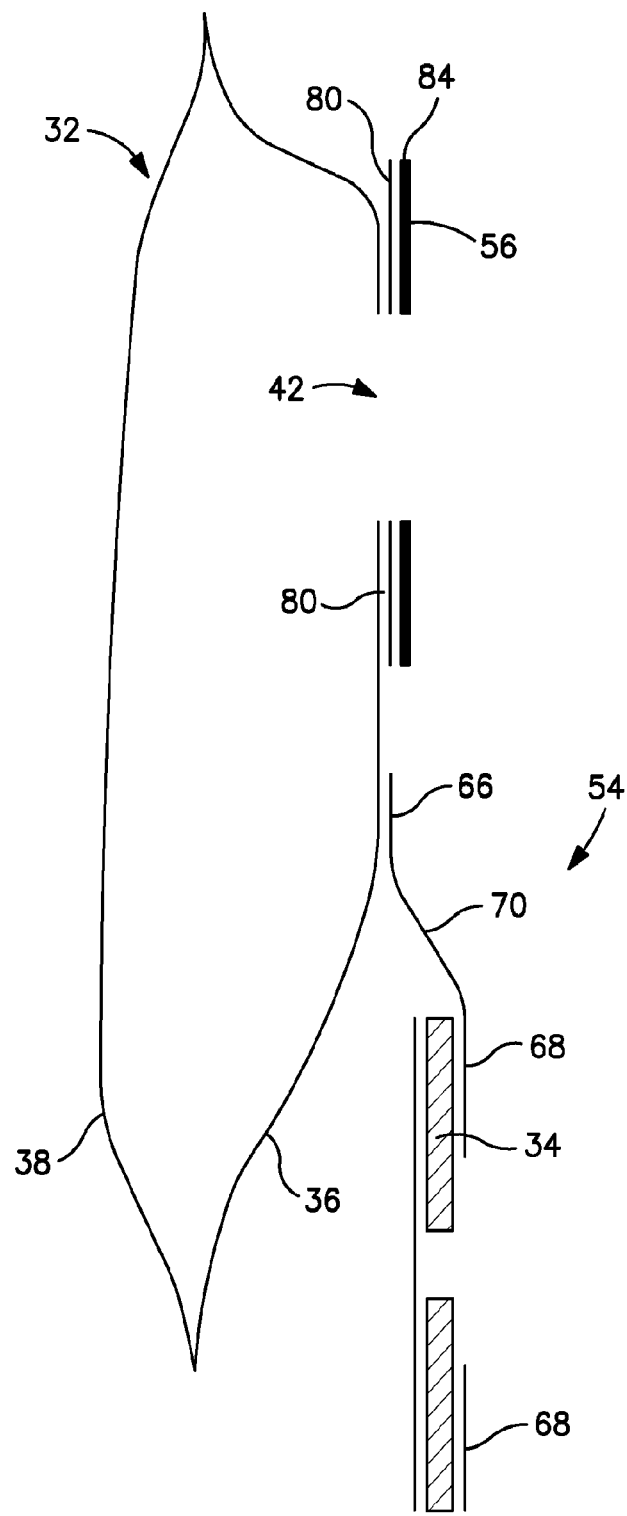
FIG. 12 is a schematic sectional view showing the third embodiment in its access position.

Referring to FIGS. 11-14, an alternative captive connection 54 has a similar folding action to that of FIGS. 1-7, except that the first attachment portion 66 for attachment to the pouch 32 has the form of a tab instead of a closed-loop shape. Two different configurations of tab are envisaged. In FIGS. 11 and 12, the joint 70 is disposed on the portion of the tab 76 facing away from the entrance aperture. In the same manner as that of FIGS. 1-7, the joint 70 is unfolded in the access position, and folds over on itself when the entrance aperture 42 and adhesive wafer 34 are in the operative, superposed position. The joint 70 unfolds as the adhesive wafer 34 is displaced away from the entrance aperture 42.

Figure 13:
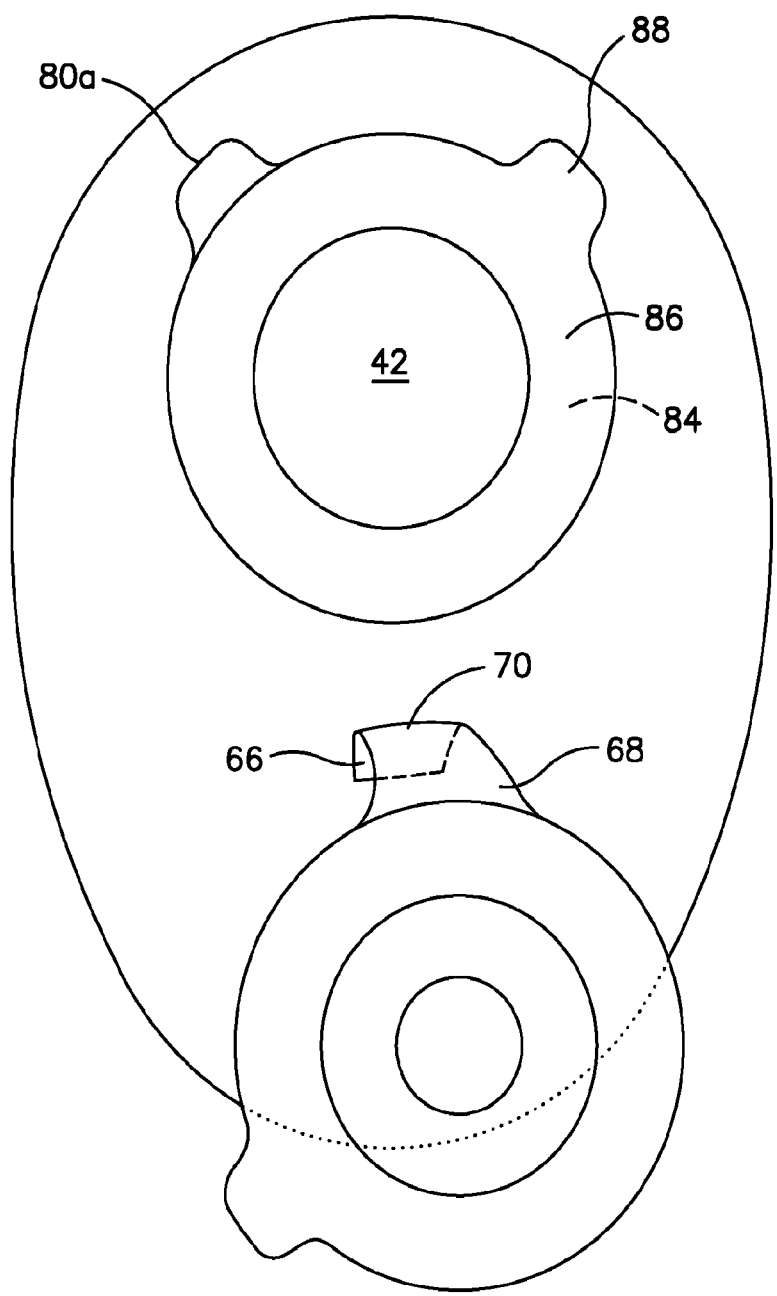
FIG. 13 is a schematic rear view showing a fourth embodiment of appliance in its access position.
Figure 14:
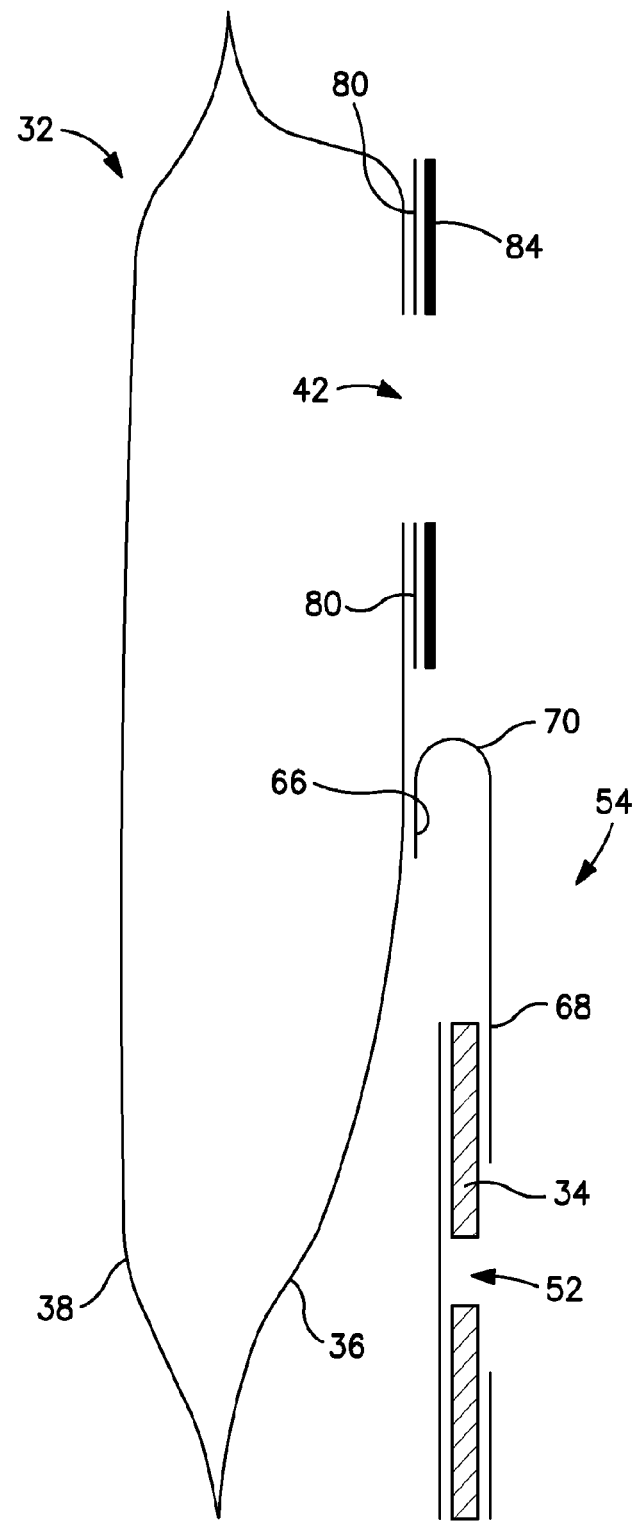
FIG. 14 is a schematic sectional view showing the fourth embodiment in its access position.

In the alternative arrangement of FIGS. 13 and 14, the joint 70 is disposed generally between the tab 76 and the entrance aperture 42. In the access position, the joint 70 is folded. In the operative, superposed position of the entrance aperture 42 and the adhesive wafer 34, the joint 70 is generally unfolded.

When a tab 76 is used, an additional reinforcing member 80 may be provided encircling the entrance aperture 42. The reinforcing member 80 may have a tab 80a to aid manipulation of the pouch 32. The reinforcing member 80 is made of a material having a greater flexural modulus than the material of the pouch wall 36, 38, so as to protect the pouch wall 36, 38 against wrinkling, and facilitate a good seal around the entrance aperture 42.

The fixation coupling 56 may be adhesive or a mechanical coupling. The fixation coupling 56 may be of a permanent type such that the fixation coupling 56 is not intended to be separated (nor re-fastened) after the initial fastening together. Alternatively, the fixation coupling 56 may be of a separable and re-fastenable type. This may permit a caregiver or nurse to temporarily open the pouch 32 away from the adhesive wafer 34, to enable inspection, cleaning, or application of medication to the stoma 60 while the adhesive wafer 34 is in situ on the body.

An adhesive coupling is currently preferred for implementing the fixation coupling 56. An adhesive coupling typically provides a lower profile height than a mechanical coupling. The adhesive coupling may use the skin-friendly adhesive of the adhesive wafer 34, or it may use a different adhesive. The adhesive coupling may comprise self-adhering films that stick to each other without being tacky.

In one form (as illustrated in all of the embodiments), the fixation coupling 56 comprises an adhesive layer 84 distinct from the wafer 34 and carried by at least one of the first and second attachment portions 66, 68 of the captive connection 54. Either both attachment portions 66, 68 may carry such adhesive, or one of the attachment portions 66, 68 may be a non-adhesive landing zone. In the form illustrated in FIGS. 2-14, the first attachment portion 66 carries the adhesive 84 and a landing surface is provided by the second attachment portion 68. However, the position of the adhesive may be reversed as desired. The adhesive layer 84 may initially be protected by a silicone or silicone-coated release sheet 86. The release sheet 86 may have a peel tab 88 that is typically spaced angularly away from the tab 66a, 80a to avoid confusion. The adhesive 84 may of the same type and/or thickness suitable for use in adhesive-coupling two-part ostomy appliances, and so does not increase significantly the thickness or profile height of the appliance 30.

Figure 16:
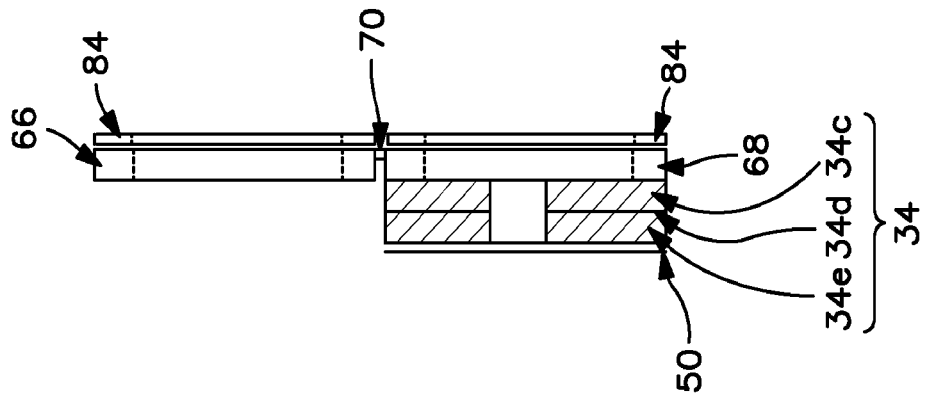
FIG. 16 is a schematic side view of the coupling assembly of FIG. 15
Figure 15:
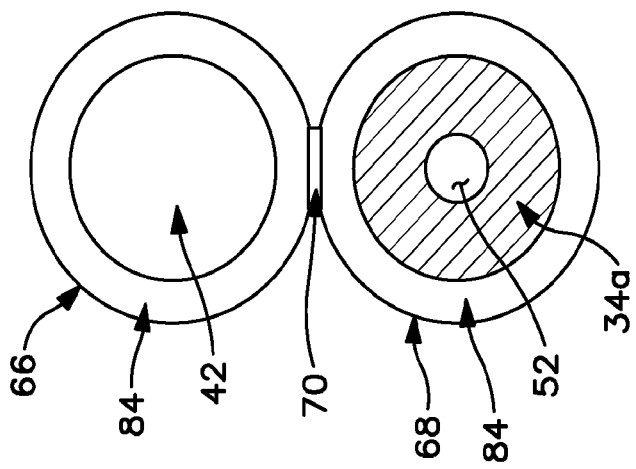
FIG. 15 is a schematic front view of a fifth embodiment of coupling assembly.

FIGS. 15 and 16 illustrate a further example of the captive connection 54 in which adhesive 84 is carried by both the first and second attachment portions 66, 68 on their respective surfaces that confront when in the operative position. These drawings also illustrate an example construction of the adhesive wafer 34, including adhesive layers 34c, 34e separated by a flexible sheet 34d providing a similar moldable characteristic as explained in the aforementioned U.S. Pat. No. 6,840,924.

In another form, the fixation coupling 56 comprises a portion of the adhesive surface of the adhesive wafer 34 on the non-body-facing side 48.

Figure 17:
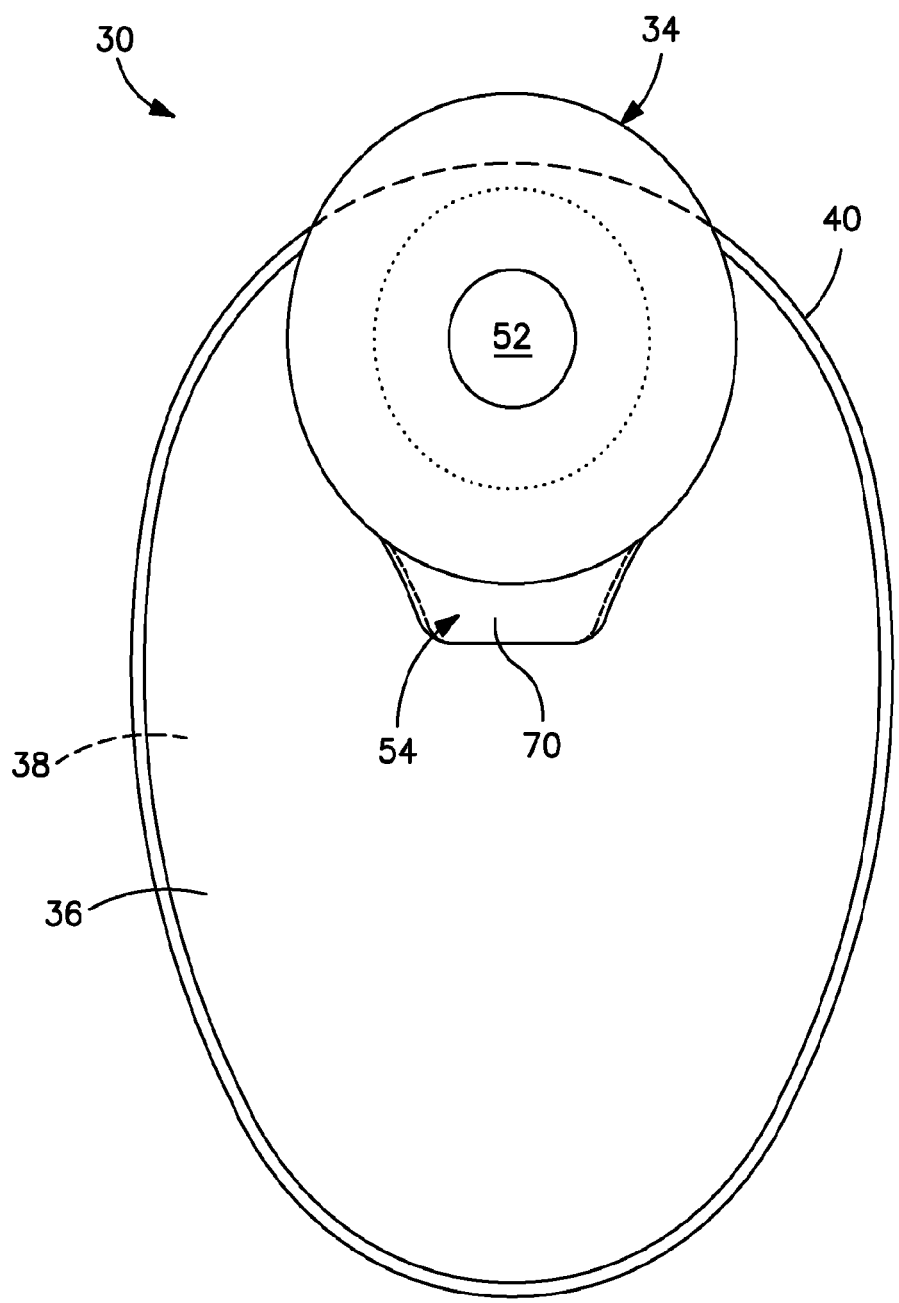
FIG. 17 is a schematic rear view showing a sixth embodiment of ostomy appliance in its operative position.

In the above embodiments, the adhesive wafer 34 is sized and positioned so that it generally lies inside the welded periphery 40 of the pouch 32. However, a further feature of the present invention is that it can provide a one-piece appliance 30 in which the adhesive wafer 34 extends all of the way up to, or even beyond, the peripheral weld 40 of the pouch 32 when the adhesive wafer 34 is in the operative condition, for example, as illustrated in FIG. 17. Such a design is possible because, the captive connection 54 permits the adhesive wafer 34 to be displaced, during manufacture, to a position in which the adhesive wafer 34 is clear of the position at which the peripheral weld 40 is to be made. This enables conventional welding equipment to approach the position of the peripheral weld 40 without being obstructed by the wafer 34. This modification may be used in combination with any of the captive connections and/or fixation couplings described herein.

The same principles discussed above may also be applied to a two piece appliance and/or to a one-piece appliance supplied in separated or "kit" form. In the case of a two-piece appliance, the fixation coupling 56 may be the conventional two-piece coupling of either an adhesive or a mechanical interference/interlock type. The first attachment portion 66 of the captive connection 54 is preferably securable, for example, releasably, to the pouch prior to aligning and securing the components of the two-piece appliance.

The above principles are now illustrated by further detailed examples:

EXAMPLE 1

An appliance 30 is made to include a pouch 32 for collecting material, an entrance aperture 42 through which material enters the pouch 32, an adhesive wafer 34 for attaching the pouch 32 to a surface where collection will be accomplished, and a coupling component 54,56 for coupling of the adhesive wafer 34 to the pouch 32.

The pouch 32 is formed by welding together two panels of film about an elliptical perimeter approximately 5 inches wide by approximately 10 inches long, one of the panels having an opening where material to be collected enters the pouch 32. A flexible, closed cell foam with thickness of approximately 0.006 inches comprised of polyethylene-co-vinyl acetate coated on one side with a polyacrylate adhesive is cut into a single shape of two adjoining rings or circles resembling the number "8" (FIG. 8). The uncoated side of one circle of the coupling (representing the first attachment portion 66) is thermally welded to a pouch film panel so that the circle encompasses the entrance aperture 42 about its entire circumference.

A hydrocolloid adhesive comprising an adhesive wafer 34 having a formulation described by any of the examples 15-25 in U.S. Pat. No. 4,551,490 is shaped into an adhesive wafer 34 approximately 0.010 inches thick with an inner diameter of approximately 10 mm and an outer diameter approximately equal to the outer diameter of the second circle of the FIG. 8 shaped coupling foam. The hydrocolloid adhesive wafer 34 is protected on one side by a coated release sheet 50. The opposite side of the hydrocolloid adhesive wafer 34 is adhered to the second circle (representing second attachment portion 68) on the uncoated side of the coupling foam. The inside diameter of the hydrocolloid adhesive wafer 34 is smaller than the inside diameter of the second attachment portion 68 to which it is adhered, and the hydrocolloid adhesive within the coupling inner diameter is protected with a second release liner 82.

In preparation for use, either or both release liners 82, 86 are removed. With the hydrocolloid adhesive now exposed it is adapted as desired for improved performance, for example, by manually adjusting the dimensions of the stomal aperture 52 to match the collection surface and improve efficient collection of material by the pouch 32.

The two circles of the FIG. 8 shaped coupling are now folded together along an axis near where they adjoin (at 70) such that the adhesive coated surface of each circle contacts the other and the adhesive wafer 34 and pouch 32 are now coupled together. The adhesive wafer 34 now indirectly abuts the entire circumference of the entrance aperture 42 via the coupling. Any remaining release liner 82, 86 is removed from the hydrocolloid adhesive wafer 34 and the adhesive wafer 34 is adhered to a surface for collection of material, for example, attaching to the skin 62 around a stoma 60 as for a one-piece appliance with a moldable adhesive.

EXAMPLE 2

A pouch 32 and adhesive wafer 34 of similar construction to those described in Example 1 above are coupled together using a self-adhering film with thickness of approximately 0.002 inches and shaped into a FIG. 8. The area where the circles are adjoined is small compared with the total area of the circles. One circle (representing first attachment portion 66) is thermally welded to the pouch film panel, the weld joint entirely encompassing the entrance aperture 42. The hydrocolloid adhesive wafer 34 is shaped into a round disc approximately 0.080 inches thick with outer diameter approximately equal to the outer diameter of the second circle of the coupling film (representing second attachment portion 68). The hydrocolloid adhesive wafer 34 is adhered to the second circle on the side of the coupling film opposite from the side welded to the pouch panel. The adhesive wafer 34 is adapted for use as described in Example 1. The two circles of the FIG. 8 shaped film coupling are now twisted and folded together along an axis near where they adjoin such that the free surfaces of each circle contact and self-adhere to one other, coupling the pouch 32 to the attachment adhesive in a manner that prevents escape of the collected material through the coupling components. The pouch 32 may be used to collect material as described in Example 1 above.

EXAMPLE 3

The pouch 32 and hydrocolloid adhesive wafer 34 of similar construction to those described in Example 1 above are coupled together using an essentially flat polyethylene vinyl acetate sheet with thickness of approximately 0.010 inches and shaped into a FIG. 8. The point of adjoining between the circles is heated and pressed to reduce its thickness and create a hinge 70 to facilitate folding or twisting. One circle (representing first attachment portion 66) is adhered with a pressure sensitive adhesive to the pouch film panel, the circle encompassing the entrance aperture 42. The hydrocolloid adhesive wafer 34 is shaped into a round disc approximately 0.040 inches thick with outer diameter equal to the outer diameter of the second circle of the FIG. 8 coupling sheet (representing the second coupling portion 68). The hydrocolloid adhesive wafer 34 is adhered to the coupling and adapted for use as described in Example 1. The two circles of the FIG. 8 shaped sheet coupling are now folded together using the hinge 70 to create contact between the circles. The pouch 32 may be used to collect material by removing the release liner 82, 86 from the hydrocolloid adhesive wafer 34 and attaching it to a surface, for example, attaching to the skin 62 around a stoma 60.

EXAMPLE 4

The pouch 32 and hydrocolloid adhesive wafer 34 of similar construction to those described in Example 1 above are coupled together using a plastic polyethylene coupling with total thickness of approximately 0.030 inches and shaped into a FIG. 8. The circumference of each circle is essentially flat and includes a sealing component comprised of corresponding surfaces that can be mechanically interlocked when brought together, for example, a raised rim and indented groove. The area of adjoining (at 70) between the circles is reduced in thickness using a routing tool creating a hinge to facilitate folding or twisting. One circle (representing first attachment portion 66) is essentially flat and thermally welded to the pouch film panel, the circle encompassing the entrance aperture 42. Attached to the outer periphery of this circle at a position approximating the circumference where it is welded to the pouch wall 36, 38 is an adhesive coated non-woven fabric. The adhesive is protected by a release liner 82, 86 and coated on the side of the fabric next to the coupling.

The hydrocolloid adhesive is shaped into an adhesive wafer 34 approximately 0.040 inches thick with outer diameter approximately equal to the outer diameter of the second circle of the FIG. 8 plastic coupling (representing the second attachment portion). The hydrocolloid adhesive wafer 34 is adhered to the second circle on the same side of the coupling as is welded to the pouch wall 36, 38. In this case the plastic coupling is shaped to facilitate adhesion to a recessed surface by imparting a convex shape to the plastic part such that it juts out away from the entrance aperture 42 when the coupling is in its final configuration. The hydrocolloid adhesive wafer 34 being adhered to the convex shaped portion of the coupling takes on that convex shape.

The hydrocolloid adhesive wafer 34 is adhered to the coupling and adapted for use as described in Example 1. The two circles of the FIG. 8 shaped sheet coupling are now folded together using the hinge 70 to facilitate contact between the circles. The coupling is now secured in its final orientation by an interlocking mechanism (representing a mechanical fixation coupling 56), for example, by inserting the raised rim of one side of the coupling into the corresponding indented groove of the other side of the coupling. The pouch 32 may be used to collect material by removing the release liner from the hydrocolloid adhesive wafer 34 and attaching it to a surface, for example, attaching to the skin 62 around a stoma 60. The pouch 32 is now made further secure to the surface where collection will be made by adhering the adhesive coated fabric onto the same surface where the hydrocolloid adhesive wafer 34 is attached.

EXAMPLE 5

The appliance 30 including the pouch 32 and hydrocolloid adhesive wafer 34 of similar construction to those described in Example 1 above are coupled together using a coupling of two discreet ring shaped attachment portions 66, 68 attached together using a rivet 72 such that the attachment portions 66, 68 may be freely rotated from an at least partially non-concentric position to a substantially concentric final position. Through this rotation they are made to adjoin across communicating surfaces and align with the pouch entrance aperture 42. One ring of the coupling (representing first attachment portion 66) is attached to the pouch 32 on one surface opposite the communicating surface, and the other ring (representing second attachment portion 68) of the coupling is attached to the hydrocolloid adhesive wafer 34 on another surface opposite the communicating surface. A coupling adhesive or gasket material on one or both communicating surfaces maintains the coupling in its final position and aids in the retention of collected material.

EXAMPLE 6

The appliance 30 including the pouch 32, hydrocolloid adhesive wafer 34 and coupling components of similar construction to those described in Example 5 above are coupled together using a rivet 74 such that the coupling components may be freely rotated from an at least partially non-concentric position to a substantially concentric final position. Through this rotation they are made to adjoin across communicating surfaces and align with the entrance aperture 42. One ring of the coupling (representing first attachment portion 66) is attached to the pouch 32 on one surface opposite the communicating surface, and the other ring of the coupling (representing second attachment portion 68) is attached to the hydrocolloid adhesive wafer 34 on another surface opposite the communicating surface. In this example the diameters of the pouch coupling ring are designed larger than those of the hydrocolloid adhesive wafer coupling ring such that the outer diameter of the latter entirely fits inside the inner diameter of the former. When rotated into its final configuration the hydrocolloid adhesive wafer coupling ring is inserted into the pouch adhesive coupling ring in a substantially coplanar configuration with the result that the hydrocolloid adhesive wafer 34 attaches to the collection surface on one side and to both coupling rings on the opposite side.

EXAMPLE 7

The appliance 30 including the pouch 32 and hydrocolloid adhesive wafer 34 of similar construction to those described in Example 1 above are coupled together using a coupling comprised of a flexible, closed cell foam with thickness of approximately 0.006 inches comprised of polyethylene-co-vinyl acetate coated on one side with a polyacrylate adhesive. The polyacrylate adhesive is protected with a release liner 82, 86 prior to use. The coupling is cut into a single annular shape that is attached to the pouch wall 36, 38 with the entrance aperture 42 via a tabbed area 76 extending radially from the outer diameter of the coupling ring between the coupling ring and the entrance aperture 42. The uncoated side of the coupling is adhered to the hydrocolloid adhesive wafer 34. The adhesive wafer 34 is then adapted as described in Example 1. The coupling is then folded across the tab 76 so that exposed polyacrylate adhesive attaches to the pouch 32 and encompasses the entrance aperture 42 about its entire circumference. Any remaining release liner 82, 86 is removed from the hydrocolloid adhesive wafer 34 and the adhesive wafer 34 is adhered to a surface for collection of material, for example, attaching to the skin 62 around a stoma 60 as for a one-piece appliance with a moldable adhesive.

Alternatively, the tabbed portion 76 of the coupling may be on the opposite side of the coupling ring form the entrance aperture 42. In this case adaptation of the hydrocolloid adhesive wafer 34 is accomplished by deflecting the tab 76 so that access to either surface of the hydrocolloid adhesive wafer 34 is easily attained. Once the hydrocolloid adhesive wafer 34 is adapted the polyacrylate adhesive coated surface of the coupling is adhered to the pouch 32 about the entrance aperture 42.

As a further option the area around the entrance aperture 42 may be reinforced to facilitate handling by attachment of an adhesive wafer 34 around the entire circumference of the entrance aperture 42, the reinforcing component having a flexural modulus exceeding that of the pouch panel material.

EXAMPLE 8

The appliance 30 including the pouch 32 and hydrocolloid adhesive wafer 34 of similar construction to those described in Example 1 above including a coupling comprised of a flexible film, foam, non-woven or other sheet of flexible material with a minimum thickness of approximately 0.002 inches and shaped into a FIG. 8. The coupling is coated on one side with at least 0.001 inch thick pressure sensitive adhesive coating that is protected with release liner 82, 86 prior to use.

The area where the circles are adjoined is small compared with the total area of the circles. One circle (representing the first attachment portion 66) is thermally welded to the pouch wall 36, 38, the weld joint entirely encompassing the entrance aperture 42. The hydrocolloid adhesive wafer 34 is shaped into a round disc approximately 0.050 inches thick with both outer and inner diameters approximately equal to those of the second circle of the coupling. The hydrocolloid adhesive wafer 34 is adhered to the second circle on the side of the coupling opposite from the side welded to the pouch wall 36, 38. The adhesive together with the coupling is adapted for use as described in Example 1 with the advantage being that the hydrocolloid adhesive wafer 34 facing the interior of the pouch 32 is now further protected from the collection material in the area where it is covered by the coupling. The two circles of the FIG. 8 shaped coupling are now twisted and folded together along an axis near where they adjoin such that the free surfaces of each circle contact one other coupling the pouch 32 to the adhesive wafer 34 in a manner that prevents escape of the collected material through the coupling components. The pouch 32 may be used to collect material as described in Example 1 above.

EXAMPLE 9

The appliance 30 including the pouch 32, hydrocolloid adhesive wafer 34 and coupling components of similar construction to those described in Example 7 above are coupled together using self-adherent materials that resist stomal effluent. A foam ring coated with a silicone coating having a probe tack less than 50 grams, force, as measured by the method described above, is attached on the uncoated side about the entire circumference of the entrance aperture 42 by a thermal weld. A non-pressure sensitive adhesive sheet that is approximately 0.010 inch thick and comprised of polyethylene vinyl acetate or a flexible thickness of polyester sheet is cut into a tabbed ring and thermally welded to the pouch wall 36, 38 having the entrance aperture 42. The adhesive wafer 34 is then adapted as described in Example 1. One side of the tabbed ring is adhered to the hydrocolloid adhesive wafer 34 and the opposite side is brought into contact with the silicone coating. Any remaining release liner 82, 86 is removed from the hydrocolloid adhesive wafer 34 and the adhesive wafer 34 is adhered to a surface for collection of material, for example, attaching to the skin 62 around a stoma 60 as for a one-piece appliance with a moldable adhesive.

It will be appreciated that many modifications, improvements and equivalents may be made within the claimed scope of the invention.

We claim:

1. A one-piece ostomy appliance comprising:
   an ostomy pouch having an entrance aperture for communicating with a stoma;
   an adhesive wafer for mounting on the body around a stoma, the adhesive wafer including a body-facing side for contacting a user's skin, a non-body-facing side opposite the body-facing side, and a moldable region for molding around a stoma;
   a fixation coupling that is permanently connected to the ostomy pouch; and
   a captive connection permanently joining the adhesive wafer to the fixation coupling, thereby joining the adhesive wafer to the ostomy pouch,
   wherein the captive connection comprises a bendable, hinged, or pivotable joint that permits relative displacement between the fixation coupling and substantially the entire adhesive wafer, the captive connection defining a range of captive movement between the pouch and the adhesive wafer, the captive range of movement including:
   (i) a superposed operative position in which the adhesive wafer is superposed around the entrance aperture while the bendable, hinged, or pivotable joint is distant from the superposed adhesive wafer; and the moldable region of the adhesive wafer is shrouded on the non-body-facing side by the pouch; and
   (ii) an access position in which the adhesive wafer is displaced about 180 degrees away from the entrance aperture of the pouch to provide access from the non-body-facing side to the moldable region of the adhesive wafer for molding the moldable region substantially without obstruction by the pouch, wherein the captive connection is present in the ostomy appliance in the superposed operative position and in the access position.

2. The one-piece ostomy appliance of claim 1, wherein the captive connection is a limited motion connection for guiding relative displacement between the adhesive wafer and the entrance aperture.

3. The one-piece ostomy appliance of claim 1, wherein captive connection comprises a first attachment portion attached to the pouch, a second attachment portion attached to the adhesive wafer, and a movable joint portion between the first and second attachment portions.

4. The one-piece ostomy appliance of claim 3, wherein at least one of the first and second attachment portions has a closed loop shape.

5. The one-piece ostomy appliance according to claim 3, wherein the first and second attachment portions and the joint portion are integrally formed as a unitary piece.

6. The one-piece ostomy appliance according to claim 3, wherein the first and second attachment portions are separate pieces movably connected at the joint portion.

7. The one-piece ostomy appliance according to claim 3, wherein the first and second attachment portions are made of plastics film.

8. The one-piece ostomy appliance according to claim 1, wherein the fixation coupling for fixing the adhesive wafer to the pouch in the superposed operative position, wherein the fixation coupling is selected from: a mechanical coupling; an adhesive coupling.

9. The one-piece ostomy appliance according to claim 2, wherein the fixation coupling for fixing the adhesive wafer to the pouch in the superposed operative position, wherein at least a portion of the fixation coupling is integral with at least a portion of the limited motion connection.

10. The one-piece ostomy appliance according to claim 1, wherein the captive connection permanently joins the adhesive wafer to the fixation coupling, thereby joining the adhesive wafer to the ostomy pouch, both before and after molding the moldable region around the stoma.

* * * * *